United States Patent
Li et al.

(10) Patent No.: US 10,422,746 B2
(45) Date of Patent: Sep. 24, 2019

(54) NANOSCALE SURFACE WITH NANOSCALE FEATURES FORMED USING DIFFUSION AT A LINER-SEMICONDUCTOR INTERFACE

(71) Applicant: International Business Machines Corporation, Armonk, NY (US)

(72) Inventors: Juntao Li, Cohoes, NY (US); Kangguo Cheng, Schenectady, NY (US); Qing Cao, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 27 days.

(21) Appl. No.: 15/840,393

(22) Filed: Dec. 13, 2017

(65) Prior Publication Data

US 2019/0178798 A1     Jun. 13, 2019

(51) Int. Cl.

| | |
|---|---|
| *G01J 3/44* | (2006.01) |
| *G01N 21/552* | (2014.01) |
| *G01N 21/65* | (2006.01) |
| *C23C 14/04* | (2006.01) |
| *B82Y 15/00* | (2011.01) |
| *G02B 5/00* | (2006.01) |
| *C23C 14/54* | (2006.01) |

(52) U.S. Cl.
CPC ............ *G01N 21/554* (2013.01); *B82Y 15/00* (2013.01); *C23C 14/044* (2013.01); *C23C 14/543* (2013.01); *G01J 3/44* (2013.01); *G01N 21/658* (2013.01); *G02B 5/008* (2013.01)

(58) Field of Classification Search
CPC ............... G01N 21/65; G01N 21/658; G01N 2021/656; G01J 3/44; G01J 3/02
USPC ........................................................ 356/301
See application file for complete search history.

(56) References Cited

U.S. PATENT DOCUMENTS

| | | |
|---|---|---|
| 6,960,528 B2 | 11/2005 | Chen et al. |
| 7,245,370 B2 | 7/2007 | Bratkovski et al. |
| 8,452,369 B2 | 5/2013 | Huys et al. |
| 8,865,402 B2 | 10/2014 | Zhang |
| 8,898,811 B2 | 11/2014 | Jen et al. |
| 9,080,981 B2 | 7/2015 | Bond et al. |
| 9,176,065 B2 | 11/2015 | Bond et al. |
| 9,267,919 B1 | 2/2016 | Larkins et al. |

(Continued)

OTHER PUBLICATIONS

G.V. Naik et al., "Alternative Plasmonic Materials: Beyond Gold and Silver," Advanced Materials, Jun. 20, 2013, pp. 3264-3294, vol. 25, No. 24.

*Primary Examiner* — Md M Rahman
(74) *Attorney, Agent, or Firm* — Vazken Alexanian; Ryan, Mason & Lewis, LLP (57) ABSTRACT

A method of forming a semiconductor structure includes patterning one or more fin structures disposed over a top surface of a substrate, a given one of the fin structures comprising a first semiconductor layer comprising a first material disposed over the top surface of the substrate and a second semiconductor layer comprising a second material disposed over a top surface of the first semiconductor layer. The method further includes forming a liner over the one or more fin structures, and performing an anneal process to form one or more nanoscale features in a top surface of the second semiconductor layer. The second material exhibits enhanced diffusion, relative to the first material, at an interface of the liner and sidewalls of the given fin structure.

13 Claims, 8 Drawing Sheets

(56) References Cited

U.S. PATENT DOCUMENTS

| | | |
|---|---|---|
| 9,395,304 B2 | 7/2016 | Yang et al. |
| 2004/0056271 A1 | 3/2004 | Chen et al. |
| 2010/0081278 A1* | 4/2010 | Hussain ................ B82Y 10/00 438/666 |
| 2013/0236881 A1 | 9/2013 | Spatz et al. |
| 2015/0053261 A1 | 2/2015 | Tsuchiya et al. |
| 2016/0104706 A1* | 4/2016 | Xu .................... H01L 29/66795 257/192 |
| 2017/0370836 A1* | 12/2017 | Gerion ................ G01N 21/253 |
| 2018/0197783 A1* | 7/2018 | Ching ................ H01L 29/785 |

\* cited by examiner

NANOSCALE SURFACE WITH NANOSCALE FEATURES FORMED USING DIFFUSION AT A LINER-SEMICONDUCTOR INTERFACE

BACKGROUND

The present application relates to semiconductors, and more specifically, to techniques for forming semiconductor structures. Surface-Enhanced Raman Scattering or Surface-Enhanced Raman Spectroscopy (SERS) is a sensing technique capable of providing detection of molecules adsorbed on metal surfaces. Raman enhancement may be provided from localized spots in metallic nanostructures due to concentrated electromagnet near-field associated with localized surface plasmon resonance of metallic nano-constructs. SERS can be performed on electrochemically roughened metal surfaces, and can be used for trace detection of chemical and biological analytes.

SUMMARY

Embodiments of the invention provide techniques for forming a nanoscale surface for SERS applications.

In one embodiment, a method of forming a semiconductor structure comprises patterning one or more fin structures disposed over a top surface of a substrate, a given one of the fin structures comprising a first semiconductor layer comprising a first material disposed over the top surface of the substrate and a second semiconductor layer comprising a second material disposed over a top surface of the first semiconductor layer. The method further comprises forming a liner over the one or more fin structures, and performing an anneal process to form one or more nanoscale features in a top surface of the second semiconductor layer. The second material exhibits enhanced diffusion, relative to the first material, at an interface of the liner and sidewalls of the given fin structure.

In another embodiment, a semiconductor structure comprises a substrate, one or more fin structures disposed over a top surface of the substrate, an isolation layer disposed over the top surface of the substrate surrounding each of the one or more fin structures, and a metal layer disposed over the isolation layer and over the one or more fin structures. A given one of the fin structures comprises a first semiconductor layer comprising a first material disposed over the top surface of the substrate and a second semiconductor layer comprising a second material disposed over a top surface of the first semiconductor layer. The second material exhibits enhanced diffusion, relative to the first material, at an interface of a liner and sidewalls of the given fin structure. A top surface of the second layer of the given fin structure comprises one or more nanoscale features.

In another embodiment, an integrated circuit comprises a Surface-Enhanced Raman Spectroscopy (SERS) nanoscale surface. The SERS nanoscale surface comprises a substrate, one or more fin structures disposed over a top surface of the substrate, an isolation layer disposed over the top surface of the substrate surrounding each of the one or more fin structures, and a metal layer disposed over the isolation layer and over the one or more fin structures. A given one of the fin structures comprises a first semiconductor layer comprising a first material disposed over the top surface of the substrate and a second semiconductor layer comprising a second material disposed over a top surface of the first semiconductor layer. The second material exhibits enhanced diffusion, relative to the first material, at an interface of a liner and sidewalls of the given fin structure. A top surface of the second layer of the given fin structure comprises one or more nanoscale features.

DETAILED DESCRIPTION

Illustrative embodiments of the invention may be described herein in the context of illustrative methods for forming a nanoscale surface useful for Surface-Enhanced Raman Spectroscopy, along with illustrative apparatus, systems and devices formed using such methods. However, it is to be understood that embodiments of the invention are not limited to the illustrative methods, apparatus, systems and devices but instead are more broadly applicable to other suitable methods, apparatus, systems and devices.

Raman signals are inherently weak, especially when using visible light excitation. The scattering efficiency is low, so that only a small number of scattered photons are available for detection. One method to amplify weak Raman signals is to employ nanoscale roughened metal (e.g., gold (Au) or silver (Ag) surfaces), referred to as Surface-Enhanced Raman Spectroscopy (SERS). A highly localized field can be created at these roughened metal nanostructures by the surface under a laser excitation. When a molecule is absorbed or lies close to the enhanced field at the surface, a large enhancement in the Raman signal can be observed compared to conventional Raman spectroscopy, which is useful for important applications such as molecule detection. Even though SERS is a potentially powerful spectroscopy technique that allows for highly sensitive structural detection of low concentration analytes through the amplification of electromagnetic fields generated by the excitation of localized surface plasmons, many challenges emerge when attempting to use these nanostructures. For example, conventional roughened metal nanostructures (e.g., nanoparticles) are not uniformly distributed and create random Raman enhancement spots, which will adversely affect the SERS properties. Thus, a need exists for making highly ordered nanostructures capable of providing consistent SERS signals in a more controllable way.

Embodiments provide techniques for forming nanoscale surfaces useful in various applications including SERS. Advantageously, embodiments permit formation of a nanoscale roughened surface. By tuning annealing and doping conditions, insulator-semiconductor-metallic nanoscale features can be formed. Tuning annealing and doping conditions can also control the shape of the nanoscale features. In some embodiments, nanoscale features may be formed with sharp tips, enhancing field emission characteristics from these tips, such as lower turn-on voltage and higher local electric field enhancement factor, which are beneficial for field emission applications.

Illustrative processes for forming nanoscale features on a surface of a semiconductor substrate will now be described with respect to FIGS. 1-11.

Figure 1:
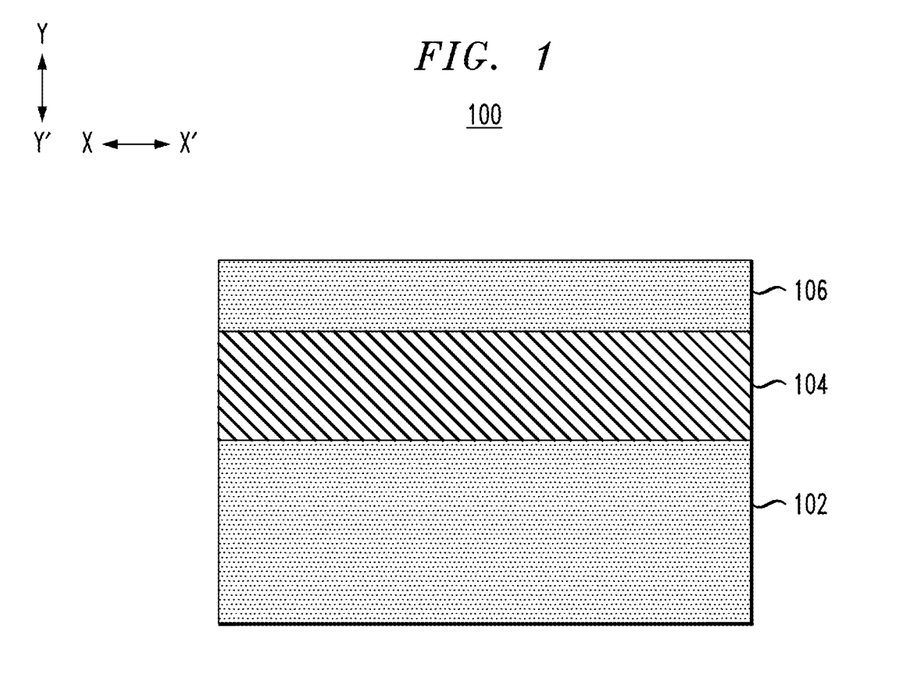
FIG. 1 depicts a side cross-sectional view of a semiconductor structure comprising first and second layers disposed over a substrate, according to an embodiment of the invention.

FIG. 1 depicts a side cross-sectional view 100 of a semiconductor structure, comprising a substrate 102 with a diffusion layer 104 and a capping layer 106 formed over a top surface thereof. In some embodiments, the substrate 102 comprises a semiconductor substrate formed of silicon (Si), although other suitable materials may be used. For example, the substrate 102 can include any suitable substrate structure, e.g., a bulk semiconductor, a semiconductor-on-insulator (SOI) substrate, etc. In one example, the substrate 102 can include a silicon-containing material. Illustrative examples of Si-containing materials suitable for the substrate 102 can include, but are not limited to, Si, silicon germanium (SiGe), silicon germanium carbide (SiGeC), silicon carbide (SiC) and multi-layers thereof. Although silicon is the predominantly used semiconductor material in wafer fabrication, alternative semiconductor materials can be employed as additional layers, such as, but not limited to, germanium (Ge), gallium arsenide (GaAs), gallium nitride (GaN), SiGe, cadmium telluride (CdTe), zinc selenide (ZnSe), etc. The substrate 102 may have a width or horizontal thickness (in direction X-X') that various, such as based on the desired size of the surface having nanoscale features formed thereon. The substrate 102 may have a height or vertical thickness (in direction Y-Y') ranging from 1 micrometer (μm) to 1 millimeter (mm).

Diffusion layer 104 may be formed of silicon germanium (SiGe), although other suitable materials may be used. The diffusion layer 104 may be doped with additional dopants. In one embodiment, the diffusion layer 104 is formed using in situ doping, an ion implantation process, plasma doping, gas phase diffusion, diffusion from a doped oxide, or a combination thereof. The conductivity type of the diffusion layer 104 can be n or p and can include different concentrations depending on the application. The diffusion layer 104 may have a height or vertical thickness (in direction Y-Y') ranging from 1 nm to 100 nm, although other thicknesses that are greater or less than this range may be employed as desired depending on the particular application.

Capping layer 106 may be formed of Si, although other suitable materials may be used. The capping layer 106 may have a height or vertical thickness (in direction Y-Y') ranging from 1 nm to 100 nm, although other thicknesses that are greater or less than this range may be employed as desired depending on the particular application.

FIG. 2 depicts a side cross-sectional view 200 of the FIG. 1 structure following patterning of fin structures 201. The fin structures 201 may be patterned after formation of a hard mask layer 108 over a top surface of the capping layer 106. The hard mask layer 108 may be formed of silicon nitride (SiN) although other suitable materials may be used. In various embodiments, the hard mask layer 108 may be an oxide such as silicon oxide (SiO), a nitride such as SiN, or an oxynitride such as silicon oxynitride (SiON), or combinations thereof. In various embodiments, the hard mask layer 108 may be silicon nitride (SiN), for example, $Si_3N_4$. The hard mask layer 108 may also be formed by a thermal process, such as, for example, oxidation or nitridation of the top semiconductor layer (e.g., oxidation or nitridation of a top portion of capping layer 106). A combination of the various processes may also be used to form the hard mask layer 108. A thin (e.g., <1 nm) oxide layer can be between the top surface of the vertical fin structures 201 and the fin hard mask layer 108. The hard mask layer 108 may have a height or vertical thickness (in direction Y-Y') ranging from 10 nm to 50 nm, although other thicknesses that are greater or less than this range may be employed as desired depending on the particular application.

The fin structures 201 may be patterned using various techniques, such as using sidewall image transfer (SIT) patterning techniques. Various types or shapes of fin structures 201 may be formed, such as an array of square or other rectangular pillars, an array of cylindrical or other rounded pillars, rectangular strips, etc. FIGS. 2B, 2C and 2D show top-down views of the FIG. 2A structure illustrating various examples of the shapes of fin structures that may be formed. FIG. 2B shows a top-down view 250 of the FIG. 2A structure, illustrating fin structures 201 formed as an array of square or rectangular pillars. FIG. 2C shows a top-down view 275 of the FIG. 2A structure, illustrating fin structures 201 formed as strips. FIG. 2D shows a top-down view 285 of the FIG. 2A structure illustrating fin structures 201 formed as cylindrical or rounded pillars. It is to be appreciated, however, that embodiments are not limited solely to the particular examples shown in FIGS. 2B-2D. For example, in some embodiments any combination of rectangular pillars, rounded pillars and stripes may be formed over the same substrate as desired.

Figure 2A:
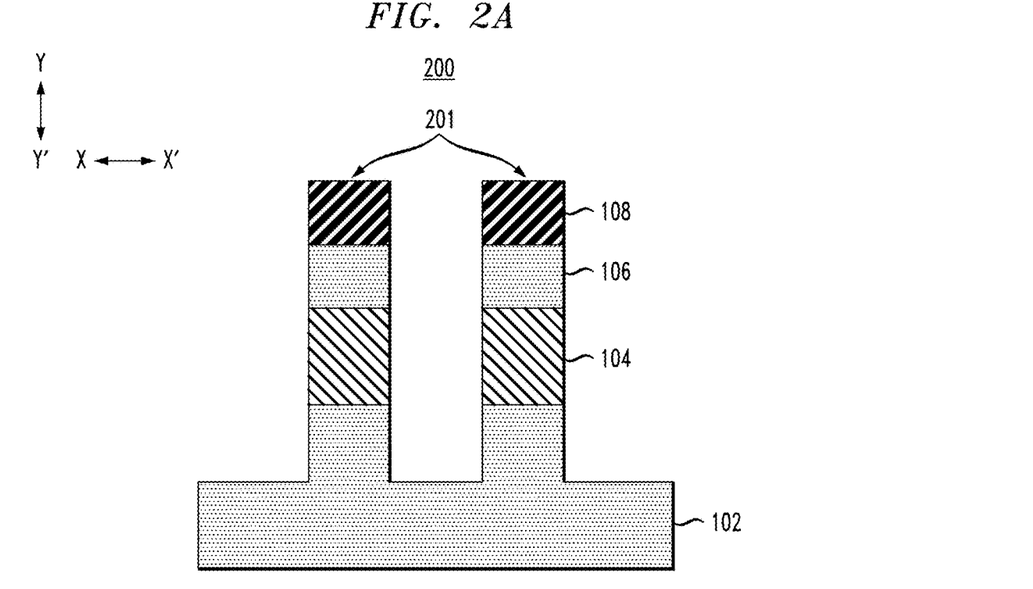
FIG. 2A depicts a side cross-sectional view of the FIG. 1 semiconductor structure following patterning of a fin array, according to an embodiment of the invention.
Figure 2B:
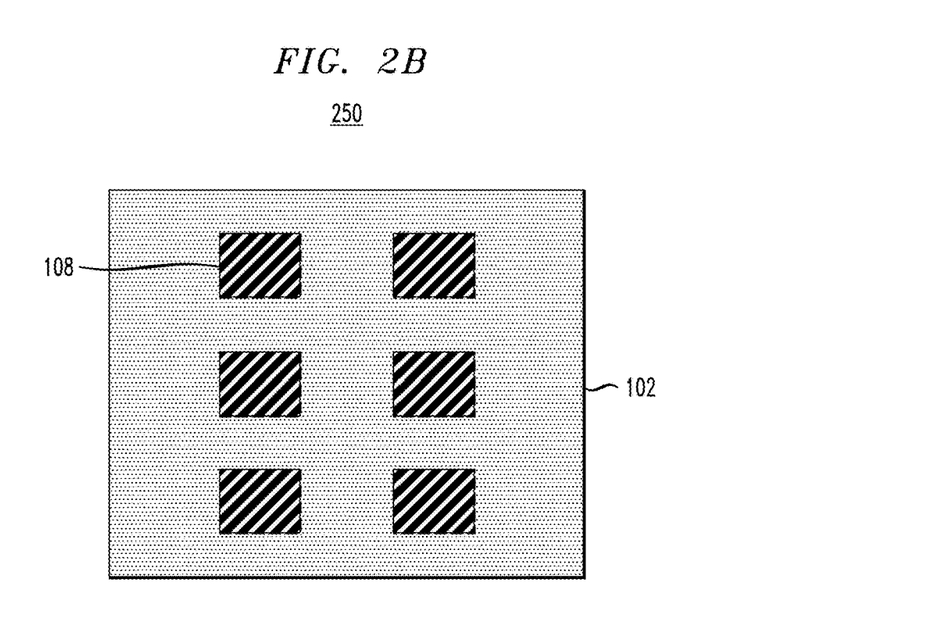
FIG. 2B depicts a top-down view of the FIG. 2A structure showing an array of rectangular fin pillars, according to an embodiment of the invention.
Figure 2C:
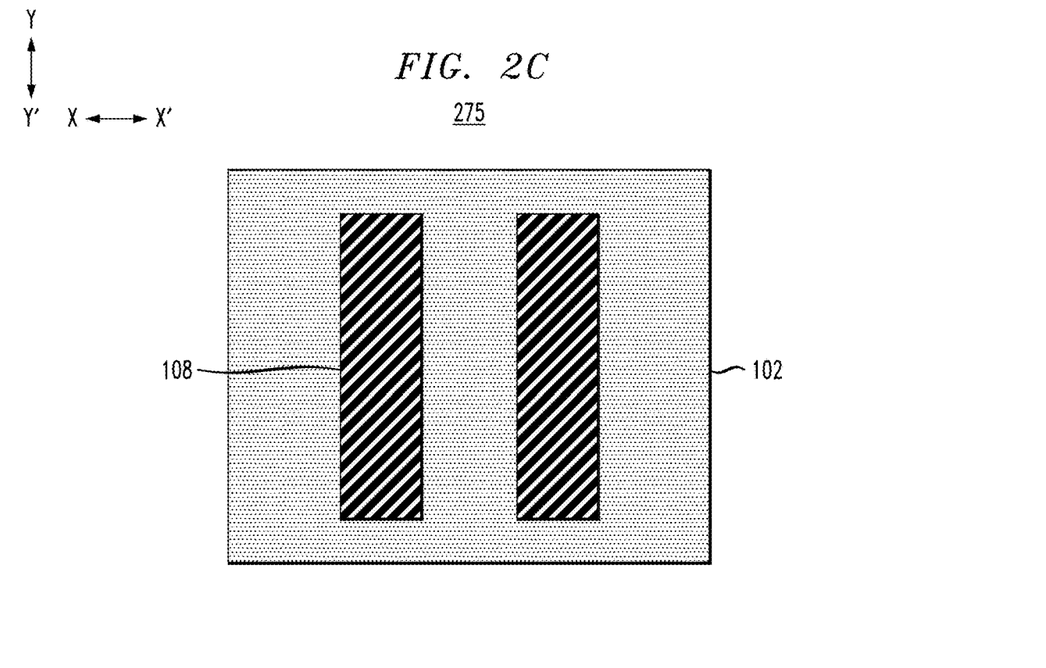
FIG. 2C depicts another top-down view of the FIG. 2A structure showing an array of fin stripes, according to an embodiment of the invention.
Figure 2D:
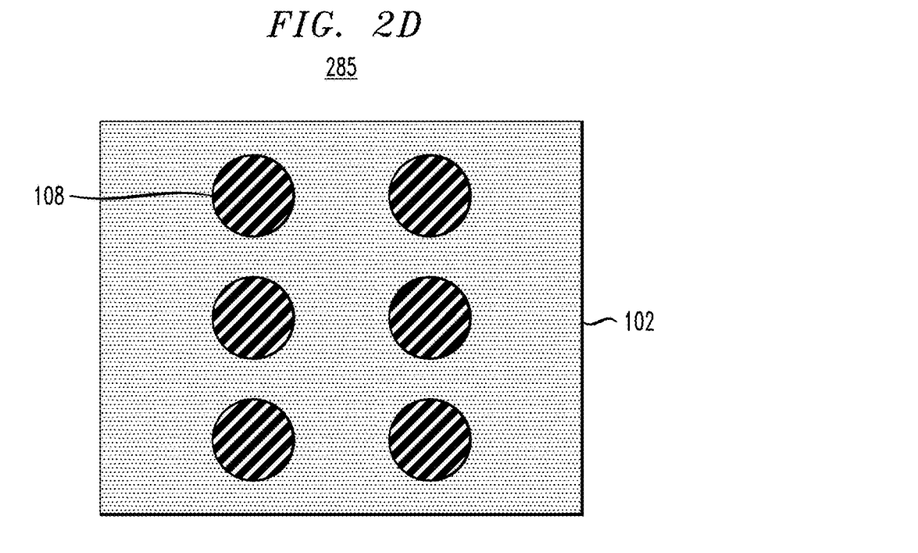
FIG. 2D depicts another top-down view of the FIG. 2A structure showing an array of rounded fin pillars, according to an embodiment of the invention.
Figure 3:
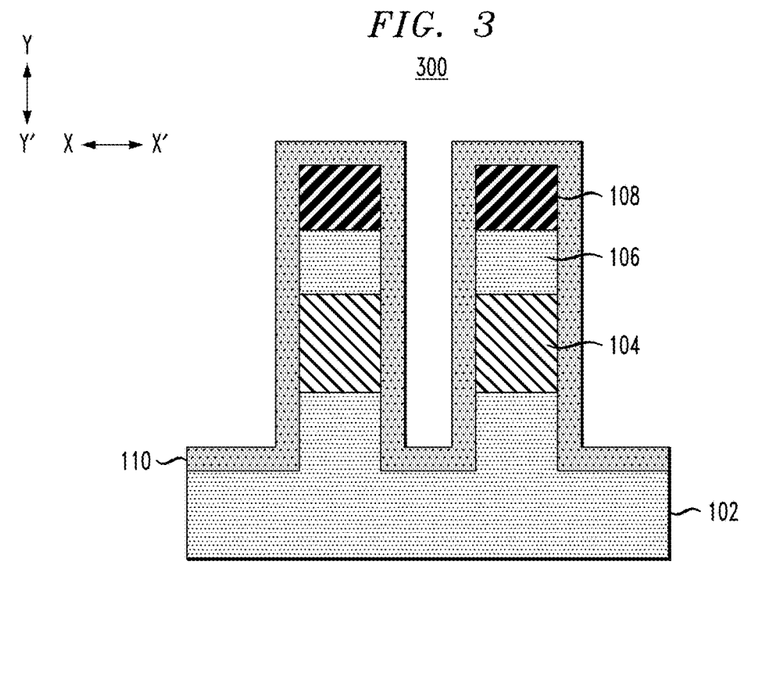
FIG. 3 depicts a side cross-sectional view of the FIG. 2A structure following deposition of a liner, according to an embodiment of the invention.

FIG. 3 depicts a side cross-sectional view 300 of the FIG. 2A structure following deposition of a liner 110 over a top surface of the substrate 102 and surrounding the fin structures 201. The liner 110 may be deposited using a conformal deposition process, such as atomic layer deposition (ALD)

or plasma-enhanced chemical vapor deposition (PECVD), although other suitable conformal deposition processes may be used. The liner 110 may comprise an oxide such as SiO, although other suitable materials may be used. The liner 110 provides oxygen in contact with diffusion layer 104 to permit oxygen diffusion from an external source such that the oxygen will react with the diffusion layer 104 as will be later described. In an alternate embodiment, the liner 110 may comprise a nitride material such as SiN, silicon carbonitride (SiCN), or another suitable material. For example, liner layer 110 may be comprised of SiN, SiCN, silicon boron nitride (SiBN), a doped nitride, SiON, etc. In some embodiments, both the patterned hard mask layer 108 and the liner layer 110 may be made of silicon nitride. The liner 110 in contact with diffusion layer 104 prevents oxygen diffusion from an external source such that the oxygen will react with the diffusion layer 104 as will be later described. The liner 110 may have a uniform thickness in the range of 3 nm to 10 nm, although other thicknesses that are greater or less than this range may be employed as desired depending on the particular application.

Figure 4:
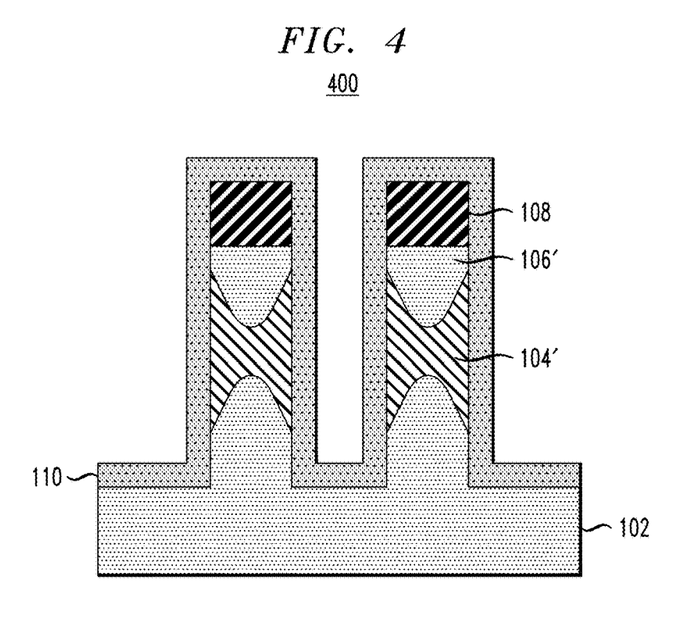
FIG. 4 depicts a side cross-sectional view of the FIG. 3 structure following an anneal process, according to an embodiment of the invention.
Figure 5:
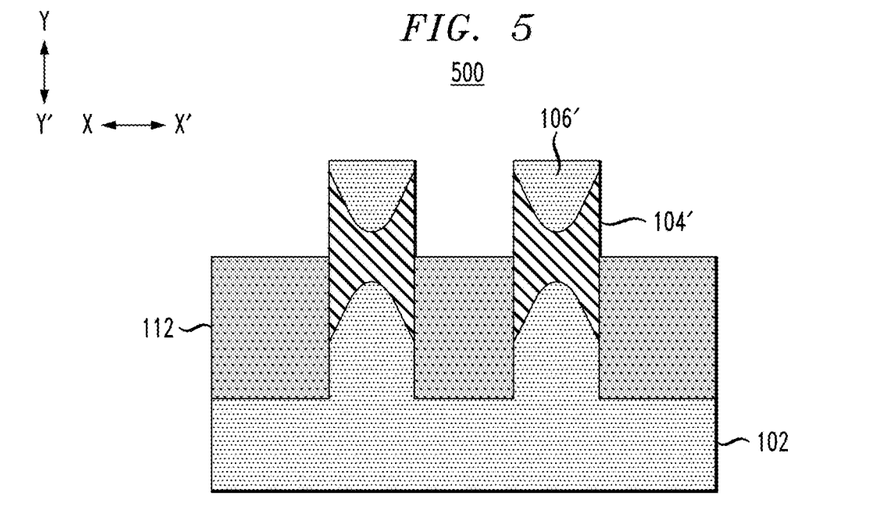
FIG. 5 depicts a side cross-sectional view of the FIG. 4 structure following fill and recess of an isolation layer, according to an embodiment of the invention.
Figure 6:
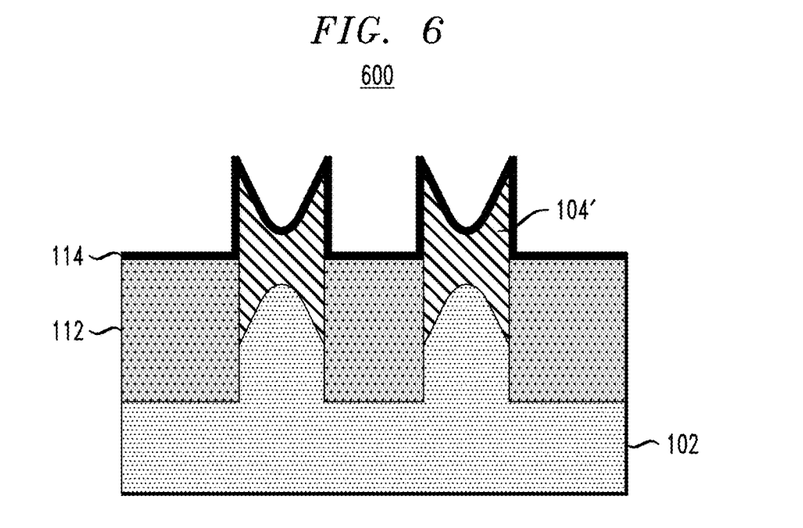
FIG. 6 depicts a side cross-sectional view of the FIG. 5 structure following removal of a capping layer and coating with a metal film, according to an embodiment of the invention.

After deposition of the liner 110, the structure of FIG. 3 may be subject to an anneal process that forms that forms an antenna or arcuate shaped feature as illustrated due to enhanced diffusion of material of the diffusion layer 104 at an interface between the liner 110 and the underlying fin structures 201. In some embodiments, the anneal process comprises annealing the structure in an inert gas, wherein the width of the fin structures 201 does not change much after the anneal process (e.g., the fin width changes less than 0.5 nm). Such embodiments are illustrated in FIGS. 4-6. In other embodiments, the anneal process comprises annealing the structure in oxygen, which trims the width of the fin structures 201 (e.g., results in reduction of fin width in the range of 5 nm to 20 nm). Such embodiments are illustrated in FIGS. 8-11.

FIG. 4 depicts a side cross-sectional view 400 of the FIG. 3 structure following annealing in an inert gas. In the description below, it is assumed that the substrate 102 and capping layer 106 are formed of Si, that the diffusion layer 104 is formed of SiGe, and that the liner 110 is an oxide, although as mentioned above various other material types may be used.

The anneal process may comprise annealing in an inert gas such as nitrogen (N), argon (Ar), hydrogen (H), a combination thereof, etc. The anneal process may be a thermal anneal, such as annealing at a temperature in the range of 600 degrees Celsius (° C.) to 1300° C., for a duration in the range of 1 nanosecond (ns) to 2 hours. Generally, higher anneal temperatures require shorter anneal times.

As mentioned above, annealing in the inert gas does not result in significant changes in the width of the fin structures 201. The particular parameters of the anneal process (e.g., concentration and type of inert gas, temperature, duration, etc.) may be tuned as desired to form a desired shape for nanoscale features. The anneal process can be furnace anneal, rapid thermal anneal, flash anneal, or any suitable combination of such processes. Typically, the lower the anneal temperature the greater difference of germanium diffusion along interface of the liner 110 and the fin versus at the interfaces between the SiGe/Si interface. The greater the diffusion difference is, the sharper the formed SiGe tips at the liner/fin interface will be.

The anneal process involves enhanced diffusion of Ge at the oxide (liner 110)-semiconductor (first layer 104 and second layer 106) interface, also referred to herein as interface enhanced diffusion. This is illustrated by the change in shape of the diffused layer 104 and capping layer 106 shown in FIG. 4 (as well as portions of the substrate that are part of the fin structures), denoted by different numerals 104' and 106', respectively. The diffused layer 104' can be used to form nanoscale features of different types, such as based on the shape of the fin structures. For square or rectangular pillars (e.g., as illustrated in the top-down view of FIG. 2B), four sharp edges or points are formed at the corners of each pillar. For strips (e.g., as illustrated in the top-down view of FIG. 2C), sharp edges on each side (e.g., "left" and "right" sides) of the strips are formed. For cylindrical or rounded pillars (e.g., as illustrated in the top-down view of FIG. 2C), a crater with sharp edges is formed for each pillar.

FIG. 5 depicts a side cross-sectional view 500 of the FIG. 4 structure following fill and recess of an isolation layer 112, and following removal of the hard mask 108 formed over each of the fin structures 201. The isolation layer 112, similar to the liner 110, may be formed of an oxide, although other suitable materials may be used. Non-limiting examples of suitable dielectric materials which may be used for the isolation layer 112 include silicon dioxide ($SiO_2$), SiN, tetraethylorthosilicate (TEOS) oxide, high aspect ratio plasma (HARP) oxide, silicon oxide (SiO), high temperature oxide (HTO), high density plasma (HDP) oxide, oxides formed by an atomic layer deposition (ALD) process, combinations thereof, etc. In some embodiments, the isolation layer 112 (also referred to as shallow trench isolation (STI) layer 112) is formed by fill of oxide over the liner 110, followed by planarization and recess.

The isolation layer 112 may have a height or vertical thickness (in direction Y-Y') ranging from 20 nm to 100 nm, although other thicknesses that are greater or less than this range may be employed as desired depending on the particular application. The thickness of isolation layer 112 may be dependent on the initial thickness of the diffusion layer 104 and capping layer 106. The isolation layer 112 should be able to protect a base region under layer 104', since a selective etch will be performed to remove the capping layer 106', which may be the same materials as the base region. Eventually, it is desired to expose the final nanostructure with sharp tips for SERS or other applications. If the final top surface location of isolation layer 112 is above the lowest portion of layer 104', the isolation layer 112 protects the base material during removal of capping layer 106'.

In some embodiments, the liner 110 may be formed of the same material as the hard mask layer 108 (e.g., SiN). If the liner 110 were not removed before recessing the isolation layer 112, a portion of the liner 110 will be left (e.g., a residual not shown in FIG. 5) on the sidewalls of the pillars after selectively removing the hard mask layer 108. The exposed portion of the liner 110 and the residual will protect the base region when the capping layer 106' is removed.

The hard mask 108 may be removed using selective etch process. The selective etch process can include, for example, fluorinated gas (such as $SF_6$, $CH_4$, or $CHF_3$) based dry etching or hot phosphoric acid ($H_3PO_4$) etching.

FIG. 6 depicts a side cross-sectional view 600 of the FIG. 5 structure following removal of the exposed capping layer 106', and following formation of a metal layer 114 over the top surface of isolation layer 112 and the exposed surfaces of the diffusion layer 104'. The exposed capping layer 106' may be removed using a selective etch, such as a selective etch which removes material of the capping layer 106' (e.g., Si) selective to material of the diffusion layer 104' (e.g., SiGe).

The metal layer 114 may be formed by coating a plasmonic metal film, and may use techniques such as atomic layer deposition (ALD). The metal layer 114 may be formed of gold (Au), silver (Ag) or another suitable material such as platinum (Pt), copper (Cu), aluminum (Al) and the like. The metal layer 114 may have a uniform thickness in the range of 1 nm to 10 nm, although other thicknesses that are greater or less than this range may be employed as desired depending on the particular application.

Figure 7:
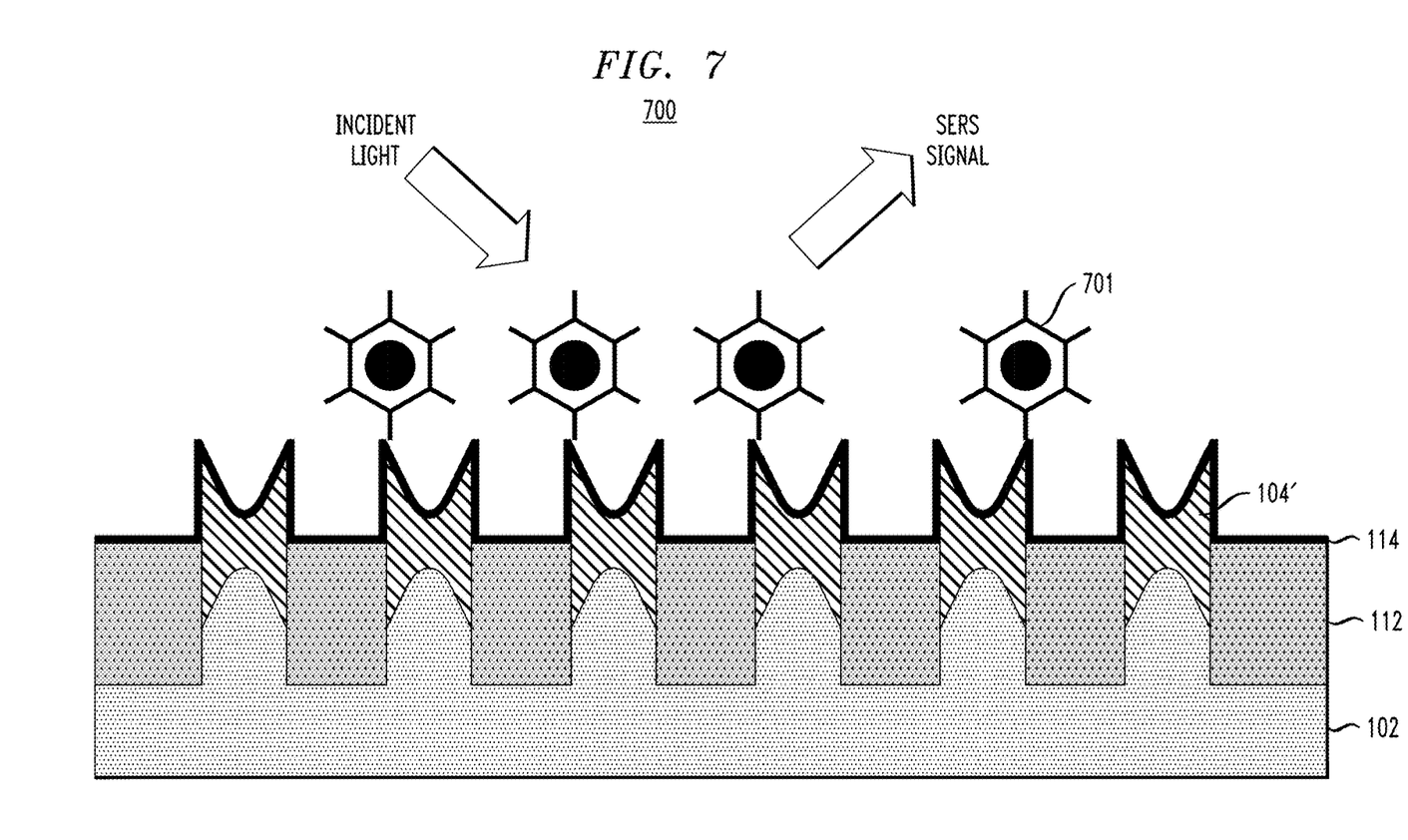
FIG. 7 depicts a side cross-sectional view of a semiconductor structure with nanoscale features formed on a surface thereof utilized for surface-enhanced Raman scattering, according to an embodiment of the invention.

FIG. 7 depicts a cross-sectional view 700 of a semiconductor structure with nanoscale features formed on a surface thereof using the techniques described above with respect to FIGS. 1-6. In FIG. 7, like reference numerals are used to denote similar elements described above with respect to FIGS. 1-6. FIG. 7 depicts an application for SERS using a substrate with nanoscale features formed on a surface thereof, such as for detecting molecules 701. Incident light is directed towards the surface with nanoscale features formed thereon, and a resulting SERS signal is reflected. The resulting SERS signal may be used to detect the type of molecules 701 present. In some embodiments, the substrate 102 may be part of an integrated circuit chip or other device in which one or more CMOS devices are also formed for detecting the resulting SERS signal, as described in further detail below with respect to FIG. 12.

As mentioned above, embodiments may use different anneal processes. FIGS. 4-6 described above illustrate the formation of nanoscale features when annealing in an inert gas. An anneal process in oxygen will now be described with respect to FIGS. 8-10.

Figure 8:
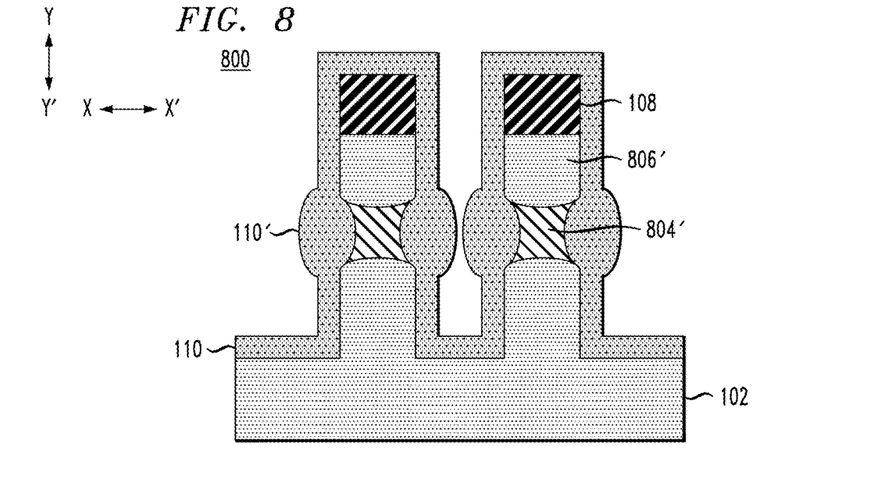
FIG. 8 depicts a side cross-sectional view of the FIG. 3 structure following another anneal process, according to an embodiment of the invention.

FIG. 8 depicts a side cross-sectional view 800 of the FIG. 3 structure following anneal in an oxidation environment, also referred to as a thermal anneal or oxidation. The oxidation may take place at a temperature in the range of 600° C. to 1300° C., with a duration in the range of 1 ns to 2 hours. It is to be appreciated, however, that other times may be employed depending on the temperature used, and on the dimensions of the nanostructures to be formed. The anneal process may be provided by at least one of a rapid thermal anneal (RTA) process, a laser-based anneal process, a flash-based anneal process or a combination thereof. The particular parameters of the oxidation (e.g., concentration of oxygen, temperature, duration, etc.) may be tuned as desired to form a desired shape for nanoscale features. The resulting shape of the nanostructures or nanoscale features depends on the anneal temperature, anneal time, oxidation rate, etc. The oxidation rate can be tuned by the concentration of the oxidation agent. For example, in a dry oxidation process where oxygen gas is used, oxygen concentration can be tuned by mixing oxygen with inert gas such as nitrogen, helium, or argon. The gas pressure is another parameter for tuning the oxidation rate. Generally, the lower oxidation rate and the higher diffusion rate difference between diffusion along the liner/fin interface vs. diffusion between Si and SiGe fin segments, the sharper the formed SiGe tips are.

Figure 11:
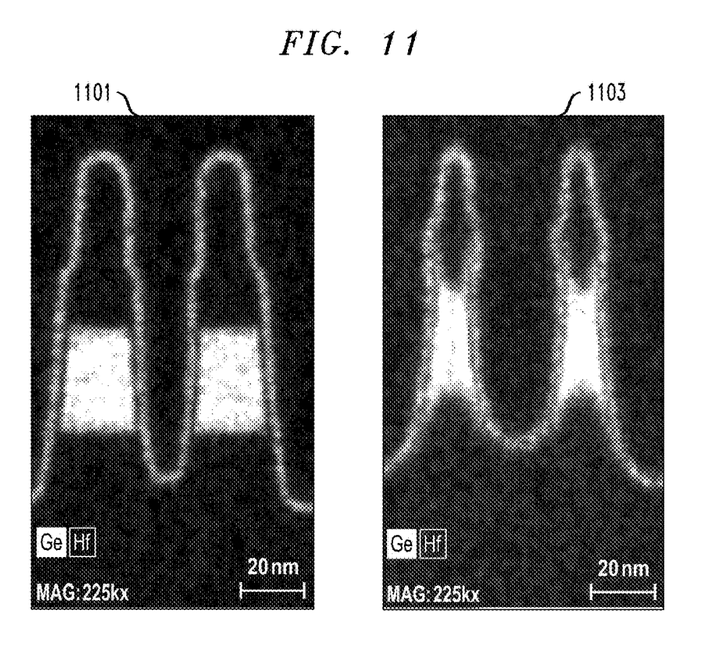
FIG. 11 depicts images of a semiconductor structure before and after an anneal process, according to an embodiment of the invention.

Similar to FIGS. 4-6, it is assumed that the substrate 102 and capping layer 106 are formed of Si, that the diffusion layer 104 is formed of SiGe, and that the liner 110 is an oxide, although other suitable materials may be used as described above. The oxidation trims the width of the fin structures 201. Illustration of trimming the fin width is shown in the images of FIG. 11, described in further detail below. The SiGe of diffusion layer 104 is oxidized faster than the Si of the substrate 102 and the capping layer 106. In addition, the Ge of diffusion layer 104 diffuses faster (e.g., relative to Si) along the oxide-semiconductor interface (e.g., the interface between liner 110 and the substrate 102, diffusion layer 104 and capping layer 106). As a result of these effects, the oxidation results in the altered shape illustrated by diffusion layer 804' and capping layer 806' in FIG. 8. This altered shape permits formation of star-like nanoscale features on the surface of the substrate 102.

Figure 9:
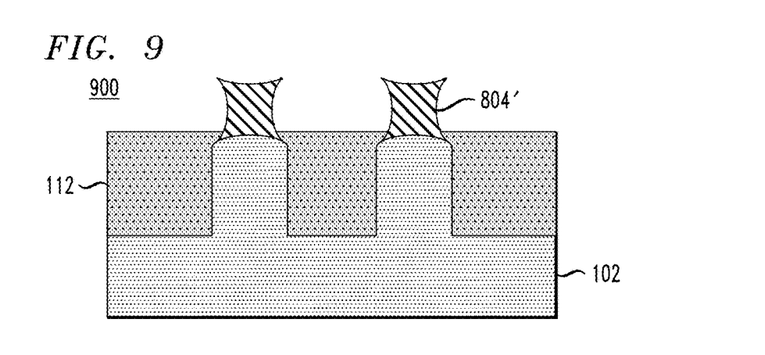
FIG. 9 depicts a side cross-sectional view of the FIG. 8 structure following fill and recess of an isolation layer, according to an embodiment of the invention.

FIG. 9 depicts a side cross-sectional view 900 of the FIG. 8 structure, following fill and recess of isolation layer 112, and following removal of the hard mask 108 and capping layer 806'. The fill and recess of isolation layer 812 is similar to that described above with respect to the fill and recess of isolation layer 112 in FIG. 5, although the isolation layer 112 may have a smaller height or vertical thickness (in direction Y-Y') relative to the isolation layer 112. As shown in FIG. 5, the isolation layer 112 has a height that extends above a bottommost surface of the capping layer 104'. In contrast, the isolation layer 112 has a height that is at or below a bottommost surface of capping layer 804'. The final top surface of the isolation layer 112 is at a position such that the top of the nanostructures and sharp tips are exposed. Assuming the liner 110 is removed prior to removal of capping layer 804', the final top surface of the isolation layer 112 will be above a lowest position of the diffusion layer 804' as described above. The hard mask 108 and capping layer 806' in FIG. 9 may be removed using processing similar to that described above with respect to FIGS. 5 and 6.

Figure 10:
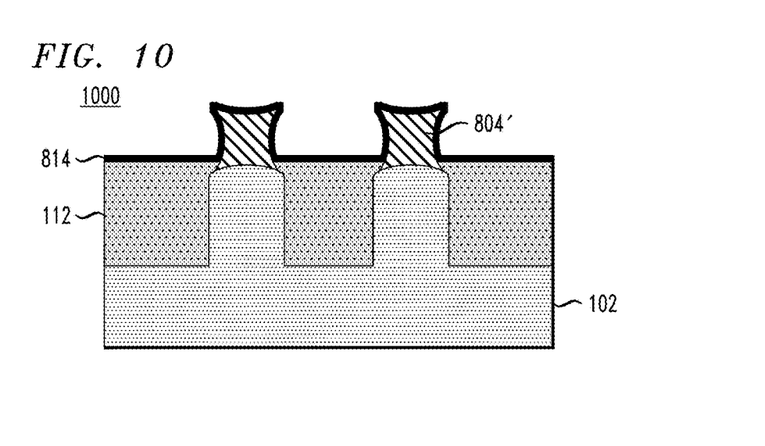
FIG. 10 depicts a side cross-sectional view of the FIG. 9 structure following removal of a capping layer and coating with a metal film, according to an embodiment of the invention.

FIG. 10 depicts a side cross-sectional view 1000 of the FIG. 9 structure, following formation of metal layer 814. The metal layer 814 may be formed using processing similar to that described above with respect to formation of the metal layer 114. The metal layer 814 may also be formed with materials and sizing similar to that of metal layer 114.

FIG. 11 depicts images 1101 and 1103 before and after an anneal process. The images 1101 and 1103 are energy-dispersive X-ray spectroscopy (EDX) map images showing a diffusion layer of fin structures before and after an oxidation anneal process. The image 1101 shows the diffusion layer (e.g., formed of SiGe) before the anneal, and the image 1103 shows the diffusion layer with altered shape after the oxidation anneal.

As described above, if the initial shape of the fin structures 201 is cylindrical or rounded, the final resulting structure will be a crater-like sharp structure after the capping layer 106'/806' is removed. If the initial shape of the fin structures 201 is square or rectangular, the final resulting structure will be four sharp, pointy nanotip or nanoscale features at the four corners of each pillar after the capping layer 106'/806' is removed. Crater-like sharp nanoscale features provide more surface area for adsorption of molecules. Sharp pointy nanoscale features at the corners of pillars provide for increasing the density of the nanoscale features (e.g., quadrupling the density of the nanoscale features) as compared with a single pointy nanoscale structure. If the initial shape of the fin structures 201 is strips or stripes, the final resulting structure will be vertical strips with two sharp pointy edges on top of the two sidewalls thereof.

The techniques described above may be used for forming various nanoscale features on the surface of a substrate useful for various applications including SERS applications. For example, heavily-doped sharp SiGe nanotips can be used as a potential plasmonic material for SERS application. For example, the dopant concentration may be in the range of 1E18 atoms/$cm^3$ to 5E22 atoms/$cm^3$. N-type dopants may be selected from a group of phosphorus (P), arsenic (As) and antimony (Sb), and p-type dopants may be selected from a group of boron (B), gallium (Ga), indium (In), and thallium (Tl). Dopants can be incorporated in the fin before, during, or after the epitaxy process. Doping techniques include ion implantation, gas phase doping, plasma doping, plasma immersion ion implantation, cluster doping, infusion doping, liquid phase doping, solid phase doping, etc. In some embodiments, dopants are preferably incorporated into fin structures by in-situ epitaxy. Dopants may be used to enhance oxidation rates. Thus, dopants (in addition to parameters such as oxidation temperature, oxidation agent concentration, etc.) may be taken into account when selecting the oxidation process to from a desired nanostructure or nanoscale features.

Sharp tips resulting from such pillars can yield extraordinary field enhancements, and the Raman scattering intensity from molecules located in the vicinity of the metallic nanosurface (e.g., metal layers 114/814) excited by light can be strongly enhanced allowing for highly sensitive detection of low concentration analytes and molecules.

Pointy and sharp tip nanoscale features also provide advantages in applications such as field emission array. The sharp tips can be used as a field emissions array due to their high aspect ratio. This significantly increases the local electrical field at the tip position, which can lower the turn-on voltage.

Embodiments provide a number of advantages relative to conventional techniques that attempt to form sharp tips, including in controllability and process complexity. In conventional techniques, sharp tips may be formed by dry and/or wet etches, which increase process complexity. As the end point for dry and wet etches is difficult to determine, conventional techniques also suffer from poor controllability. Metal-catalyzed low-pressure chemical vapor synthetic approaches may be used to grow nanorods, nanowires and nanowhisker structures. Such approaches, however, are not cost effective. In addition, array alignment is not well controlled in such approaches due to the non-uniformity of catalyst size and pattern. Scanning focused electron or ion beams, or laser beams, can also be used to form sharp tips. Such techniques, however, are slow fabrication processes.

Some embodiments, as discussed above, use enhanced Ge diffusion at an oxide-semiconductor interface (e.g., interface enhanced diffusion), to form sharp nanotips and other nanoscale features. Enhanced Ge diffusion is simple and more controllable compared to the above-described conventional techniques. In addition, embodiments enable highly ordered arrays useful for SERS and other applications, unlike random distributions of nanoparticles provided by the above-described conventional techniques. Also, embodiments provide the potential for integrated SERS with CMOS to provide on-chip SERS solutions as illustrated in FIG. 12.

Figure 12:
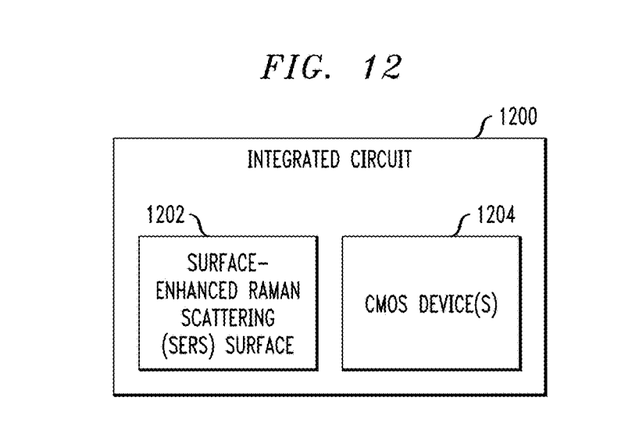
FIG. 12 depicts an integrated circuit comprising a Surface-Enhanced Raman Scattering (SERS) surface and a complementary metal-oxide-semiconductor (CMOS) devices, according to an embodiment of the invention.

FIG. 12 shows an integrated circuit 1200, with a SERS surface 1202 and one or more CMOS devices 1204. The SERS surface 1202 and CMOS devices 1204 may be formed on a common substrate in different portions thereof.

In some embodiments, a method of forming a semiconductor structure comprises patterning one or more fin structures disposed over a top surface of a substrate, a given one of the fin structures comprising a first semiconductor layer comprising a first material disposed over the top surface of the substrate and a second semiconductor layer comprising a second material disposed over a top surface of the first semiconductor layer. The method further comprises forming a liner over the one or more fin structures, and performing an anneal process to form one or more nanoscale features in a top surface of the second semiconductor layer. The second material exhibits enhanced diffusion, relative to the first material, at an interface of the liner and sidewalls of the given fin structure.

The anneal process may comprise a thermal anneal in inert gas or a thermal anneal in an oxygen-containing environment.

The given fin structure may comprise a rectangular pillar, and the one or more nanoscale features may comprise a pointed tip at each corner of the rectangular pillar. The given fin structure may alternatively comprise a cylindrical pillar, and the one or more nanoscale features may comprise a crater with a pointed edge on sidewalls of the cylindrical pillar. The given fun structure may alternatively comprise a strip, and the one or more nanoscale features may comprise a pointed vertical strip on each sidewall of the strip.

In some embodiments, the first semiconductor material comprises silicon and the second semiconductor material comprises silicon germanium.

Patterning the one or more fin structures may comprise forming the substrate, the substrate providing the first semiconductor layer of the given fin structure, forming the second semiconductor layer disposed over a top surface of the substrate, forming a third semiconductor layer disposed over a top surface of the second semiconductor layer, forming a hard mask layer disposed over a top surface of the third semiconductor layer, and performing a sidewall image transfer to form the one or more fin structures.

In some embodiments forming the liner comprises depositing an oxide liner disposed over the top surface of the substrate and the one or more fin structures. Performing the anneal process may result in diffusion of the second material at the interface of the liner and the sidewalls of the given fin structure such that the second semiconductor layer has: (i) a first height proximate sidewalls of the given fin structure; and (ii) a second height proximate a middle of the given fin structure, the first height being taller than the second height. Performing the anneal process may result in diffusion of the second material at the interface of the liner and the sidewalls of the given fin structure such that the second semiconductor layer has a height profile which decreases as distance from sidewalls of the given fin structure increases.

In some embodiments, the method further comprises removing the liner, filling isolation material over a top surface of the substrate and the one or more fin structures, recessing the isolation material below a top surface of the one or more fin structures to form an isolation layer disposed over the top surface of the substrate and surrounding the one or more fin structures, removing the hard mask layer, and removing the third semiconductor layer.

The method may further comprise forming a metal layer disposed over the one or more fin structures. The metal layer may be formed by depositing a plasmonic metal film.

In some embodiments, a semiconductor structure comprises a substrate, one or more fin structures disposed over a top surface of the substrate, an isolation layer disposed over the top surface of the substrate surrounding each of the one or more fin structures, and a metal layer disposed over the isolation layer and over the one or more fin structures. A given one of the fin structures comprises a first semiconductor layer comprising a first material disposed over the top surface of the substrate and a second semiconductor layer comprising a second material disposed over a top surface of the first semiconductor layer. The second material exhibits enhanced diffusion, relative to the first material, at an interface of a liner and sidewalls of the given fin structure. A top surface of the second layer of the given fin structure comprises one or more nanoscale features.

The given fin structure may comprise a rectangular pillar, and the one or more nanoscale features may comprise a pointed tip at each corner of the rectangular pillar. The given fin structure may alternatively comprise a cylindrical pillar, and the one or more nanoscale features may comprise a crater with a pointed edge on sidewalls of the cylindrical pillar. The given fin structure may alternatively comprise a strip, and the one or more nanoscale features may comprise a pointed vertical strip on each sidewall of the strip.

In some embodiments, an integrated circuit comprises a Surface-Enhanced Raman Spectroscopy (SERS) nanoscale surface. The SERS nanoscale surface comprises a substrate, one or more fin structures disposed over a top surface of the substrate, an isolation layer disposed over the top surface of the substrate surrounding each of the one or more fin structures, and a metal layer disposed over the isolation layer and over the one or more fin structures. A given one of the fin structures comprises a first semiconductor layer comprising a first material disposed over the top surface of the substrate and a second semiconductor layer comprising a second material disposed over a top surface of the first semiconductor layer. The second material exhibits enhanced diffusion, relative to the first material, at an interface of a liner and sidewalls of the given fin structure. A top surface of the second layer of the given fin structure comprises one or more nanoscale features. The integrated circuit may further comprise a CMOS device integrated with the SERS surface and configured to detect SERS signals from incident light directed at the SERS surface.

It is to be appreciated that the various materials, processing methods (e.g., etch types, deposition types, etc.) and dimensions provided in the discussion above are presented by way of example only. Various other suitable materials, processing methods, and dimensions may be used as desired.

Semiconductor devices and methods for forming same in accordance with the above-described techniques can be employed in various applications, hardware, and/or electronic systems. Suitable hardware and systems for implementing embodiments of the invention may include, but are not limited to, sensors an sensing devices, personal computers, communication networks, electronic commerce systems, portable communications devices (e.g., cell and smart phones), solid-state media storage devices, functional circuitry, etc. Systems and hardware incorporating the semiconductor devices are contemplated embodiments of the invention. Given the teachings provided herein, one of ordinary skill in the art will be able to contemplate other implementations and applications of embodiments of the invention.

Various structures described above may be implemented in integrated circuits. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of forming a semiconductor structure, comprising:
    patterning one or more fin structures disposed over a top surface of a substrate, a given one of the fin structures comprising a first semiconductor layer comprising a first material disposed over the top surface of the substrate and a second semiconductor layer comprising a second material disposed over a top surface of the first semiconductor layer;
    forming a liner over the one or more fin structures; and
    performing an anneal process to form one or more nanoscale features in a top surface of the second semiconductor layer, wherein the second material exhibits enhanced diffusion, relative to the first material, at an interface of the liner and sidewalls of the given fin structure;
    wherein patterning the one or more fin structures comprises:
        forming the substrate, the substrate providing the first semiconductor layer of the given fin structure;
        forming the second semiconductor layer disposed over a top surface of the substrate;
        forming a third semiconductor layer disposed over a top surface of the second semiconductor layer;
        forming a hard mask layer disposed over a top surface of the third semiconductor layer; and
        performing a sidewall image transfer to form the one or more fin structures.

2. The method of claim 1, wherein the anneal process comprises a thermal anneal in inert gas.

3. The method of claim 1, wherein the anneal process comprises a thermal anneal in an oxygen-containing environment.

4. The method of claim 1, wherein the given fin structure comprises a rectangular pillar, and wherein the one or more nanoscale features comprise a pointed tip at each corner of the rectangular pillar.

5. The method of claim 1, wherein the given fin structure comprises a cylindrical pillar, and wherein the one or more nanoscale features comprise a crater with a pointed edge on sidewalls of the cylindrical pillar.

6. The method of claim 1, wherein the given fin structure comprises a strip, and wherein the one or more nanoscale features comprise a pointed vertical strip on each sidewall of the strip.

7. The method of claim 1, wherein the first semiconductor material comprises silicon and the second semiconductor material comprises silicon germanium.

8. The method of claim 1, wherein forming the liner comprises depositing an oxide liner disposed over the top surface of the substrate and the one or more fin structures.

9. The method of claim 8, wherein performing the anneal process results in diffusion of the second material at the interface of the liner and the sidewalls of the given fin structure such that the second semiconductor layer has: (i) a first height proximate sidewalls of the given fin structure;

and (ii) a second height proximate a middle of the given fin structure, the first height being taller than the second height.

10. The method of claim 8, wherein performing the anneal process results in diffusion of the second material at the interface of the liner and the sidewalls of the given fin structure such that the second semiconductor layer has a height profile which decreases as distance from sidewalls of the given fin structure increases.

11. The method of claim 8, further comprising:
    removing the liner;
    filling isolation material over a top surface of the substrate and the one or more fin structures;
    recessing the isolation material below a top surface of the one or more fin structures to form an isolation layer disposed over the top surface of the substrate and surrounding the one or more fin structures;
    removing the hard mask layer; and
    removing the third semiconductor layer.

12. The method of claim 1, further comprising forming a metal layer disposed over the one or more fin structures.

13. The method of claim 12, wherein forming the metal layer comprises depositing a plasmonic metal film.

* * * * *